US009529009B2

(12) United States Patent
Tanoue et al.

(10) Patent No.: US 9,529,009 B2
(45) Date of Patent: Dec. 27, 2016

(54) AUTOMATIC ANALYZER

(75) Inventors: Hidetsugu Tanoue, Tokyo (JP);
Kazuhiro Tanaka, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 334 days.

(21) Appl. No.: 14/124,005

(22) PCT Filed: Jun. 4, 2012

(86) PCT No.: PCT/JP2012/064408
§ 371 (c)(1),
(2), (4) Date: Dec. 5, 2013

(87) PCT Pub. No.: WO2012/169469
PCT Pub. Date: Dec. 13, 2012

(65) Prior Publication Data
US 2014/0123774 A1 May 8, 2014

(30) Foreign Application Priority Data
Jun. 6, 2011 (JP) .................................. 2011-126427

(51) Int. Cl.
*G01N 35/10* (2006.01)
*G01F 23/26* (2006.01)

(52) U.S. Cl.
CPC ........... *G01N 35/1016* (2013.01); *G01F 23/26* (2013.01); *G01F 23/263* (2013.01);
(Continued)

(58) Field of Classification Search
CPC .................. G01N 35/1065; G01N 2035/1025; G01N 2035/1048; G01N 35/10; G01F 23/263; G01F 23/26
(Continued)

(56) References Cited

U.S. PATENT DOCUMENTS 4,912,976 A 4/1990 Labriola, II
5,365,783 A 11/1994 Zweifel
(Continued)

FOREIGN PATENT DOCUMENTS

JP 02-059619 A 2/1990
JP 08-15277 A 1/1996
(Continued)

OTHER PUBLICATIONS

European Search Report received in corresponding European Application No. 12796653 dated Oct. 13, 2014.
(Continued)

*Primary Examiner* — Peter Macchiarolo
*Assistant Examiner* — Anthony W Megna Fuentes
(74) *Attorney, Agent, or Firm* — Mattingly & Malur, PC (57) ABSTRACT

An automatic analyzer uses probes for detecting liquid levels based on a capacitance detection method. Erroneous detection of liquid levels due to interference caused by the frequency difference of oscillators is reducted. When frequencies f1 and f2 of respective detector oscillators, which are originally equal to each other, are different by approximately several Hz from each other due to a manufacturing variation, oscillation waveforms are added to liquid level detection voltages, causing a premature determination that the probes have contacted the liquid surface before actual contact therewith. By setting the difference between the frequencies f1 and f2 of the detector oscillators to be in the range of several kHz, an oscillation waveform corresponding to the difference between the frequencies is added to the detection voltages, but the amplitude values of the high-frequency components are attenuated by high-frequency attenuators, thereby ensuring accuracy in the liquid level detection.

2 Claims, 6 Drawing Sheets

(52) U.S. Cl.
CPC ....... *G01F 23/266* (2013.01); *G01N 35/1009* (2013.01); *G01N 35/1065* (2013.01); *G01N 2035/1025* (2013.01); *G01N 2035/1048* (2013.01)

(58) Field of Classification Search
USPC   73/863.01, 64.55, 290, 291, 304 C; 436/54; 340/620; 422/106
See application file for complete search history.

(56) References Cited

U.S. PATENT DOCUMENTS

| | | | |
|---|---|---|---|
| 6,551,558 | B1 | 4/2003 | Mann et al. |
| 8,863,593 | B2* | 10/2014 | Weng ................. G01N 35/1011 73/863.01 |
| 2005/0092080 | A1 | 5/2005 | Harazin et al. |
| 2007/0144253 | A1* | 6/2007 | Kobayashi .............. G01F 23/28 73/304 C |
| 2009/0133511 | A1 | 5/2009 | Heinze et al. |
| 2009/0169432 | A1 | 7/2009 | Kuroda |
| 2010/0092340 | A1 | 4/2010 | Inamura et al. |

FOREIGN PATENT DOCUMENTS

| | | |
|---|---|---|
| JP | 08-122126 A | 5/1996 |
| JP | 08-122338 A | 5/1996 |
| JP | 2003-057096 A | 2/2003 |
| JP | 2003-114239 A | 4/2003 |
| JP | 2004-045112 A | 2/2004 |
| JP | 2006-119156 A | 5/2006 |
| JP | 2007-114192 A | 5/2007 |
| JP | 2007-322286 A | 12/2007 |
| JP | 2007-322394 A | 12/2007 |

OTHER PUBLICATIONS

International Preliminary Report on Patentability received in International Application No. PCT/JP2012/064408.

* cited by examiner

AUTOMATIC ANALYZER

TECHNICAL FIELD

The present invention relates to an automatic analyzer that qualitatively and quantitatively analyzes a biological sample such as blood, urine, or the like.

BACKGROUND ART

For qualitative and quantitative analysis of target components of biological samples such as blood, urine, or the like, automatic analyzers measure the concentration by adding a reagent to the biological sample and causing the sample to biochemically react with the reagent. Since such automatic analyzers can attain improved reproducibility of measurement results and quick measurement of samples, the automatic analyzers are widely used in large hospitals, inspection centers, and the like. One of the reasons for widespread use is that the automatic analyzer employs a dispensing device capable of automatically dispensing a sample and a reagent with high accuracy at a high speed for their biochemical reaction.

In particular, a probe can be used to capture a predetermined amount of reagent or sample. In this case, variations in the amount of the reagent or the like attached to an outer wall of the probe raises the following: probabilistic carrying in of the reagent or the like to a vessel into which the reagent or the like is dispensed or to a sample vessel for the next time or later; and insufficient cleaning of the outer wall of the probe.

Then, mixing of a reagent with another reagent or mixing of a sample with another sample will lead to an increase in a variation in analysis reproducibility and an increase in cross-contamination between samples.

There is a known method for minimizing the amount of the reagent or the like attached to the outer wall of the probe and a variation in amount of the attached reagent or the like. Such a method causes a sensor to detect a liquid level, and is adapted to control the immersion depth of a probe's top end into the reagent or the sample, thereby performing dispensing with high accuracy at a high speed.

For example, an example is known in which a dispensing probe is used as one electrode for detecting a liquid level, the other electrode is used as a vessel holding stage, and the liquid level within a vessel is detected on the basis of a variation in capacitance between the electrodes. Examples of the known example include a device that uses a bridge circuit (Patent Document 1) and a device that uses a differentiating circuit (Patent Document 2).

Each of the examples described above adopts a system in which an input signal with a certain frequency component is applied to the dispensing probe.

As an example of a device capable of performing dispensing at a high speed, a high-performance analyzer (Patent Document 3) is known which has a plurality of probes and causes the plurality of probes to simultaneously dispense a reagent, thereby making it possible to perform simultaneous processing per unit time.

In addition, there is known an automatic analyzer which holds many types of reagents stored in many containers on a single reagent disk and is capable of measuring several tens of types of target components at one time (Patent Document 4).

PRIOR ART DOCUMENT

Patent Documents

Patent Document 1: JP-H8-122126-A
Patent Document 2: JP-H2-59619-A
Patent Document 3: JP-2004-045112-A
Patent Document 4: JP-2006-119156-A

SUMMARY OF THE INVENTION

Problem to be Solved by the Invention

In an automatic analyzer having a function of detecting liquid levels by a capacitance detection method, interference occurs when a plurality of probes simultaneously suck a sample or a reagent for the purpose of dispensing with high accuracy at a high speed. The interference is caused by frequency signals depending on the frequency difference between the signals from oscillators inclusive of a detector signal variation resulting in detecting a liquid level when a single probe sucks the sample or the reagent.

As a result, an actual signal change due to a variation in capacitance before and after the probe's contact to liquid surface becomes unclear to thereby cause an immersion depth variation of a probe's top end into the liquid surface of the sample or reagent or cause an erroneous detection, thus degrading the dispensing reliability.

An object of the present invention is to obtain an automatic analyzer that uses a plurality of probes to detect liquid levels based on a capacitance detection method, in which an erroneous detection of liquid levels, which is due to interference caused by the frequency difference between signals from oscillators, less occurs, so that dispensing with high accuracy at a high speed can be performed.

Means for Solving the Problem

In order to achieve the aforementioned object, the present invention is configured as follows.

An automatic analyzer that analyzes a sample includes a plurality of oscillators that each supply, to each of a plurality of dispensing probes, alternating voltages having a specific range of frequency difference therebetween; a high-frequency attenuators that are each provided for each of the plurality of oscillators and attenuate the specific range of frequency components derived from the alternating voltages of the dispensing probes; and liquid level detection determining units that determine whether or not the dispensing probes have contacted liquid surfaces of the liquid samples or liquid reagents on the basis of signals output from the high-frequency attenuators and that stop vertical movement operations of the dispensing probes if the liquid level detection determining units determine that the probes have contacted the liquid surfaces.

Effect of the Invention

There is realized an automatic analyzer that uses a plurality of probes to detect liquid levels based on a capacitance detection method, in which an erroneous detection of liquid levels, which is due to interference caused by the frequency difference between signals from oscillators, less occurs, so that dispensing with high accuracy at a high speed can be performed.

MODE FOR CARRYING OUT THE INVENTION

Hereinafter, embodiments of the present invention are described with reference to the accompanying drawings.

First Embodiment

Figure 1:
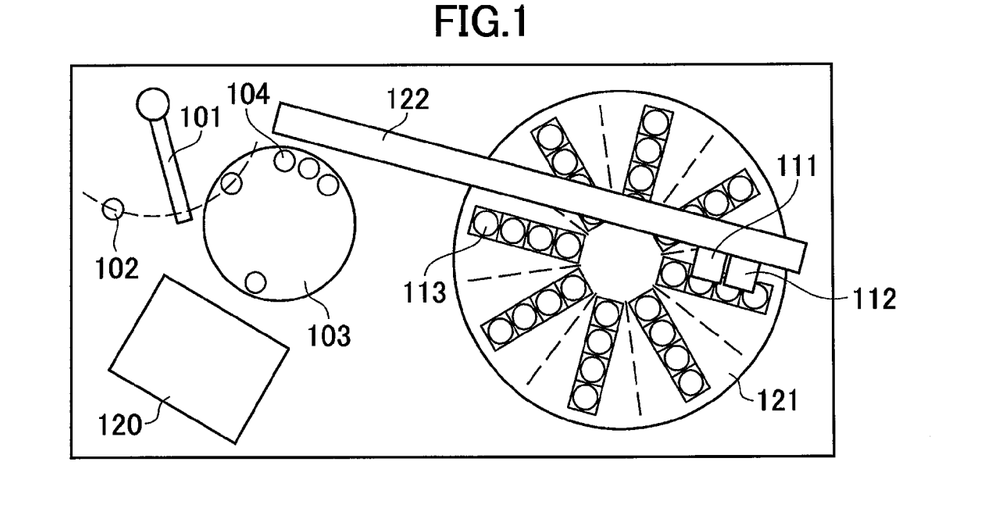
FIG. 1 is a schematic diagram illustrating the configuration of an automatic analyzer to which the present invention is applied.
Figure 2:
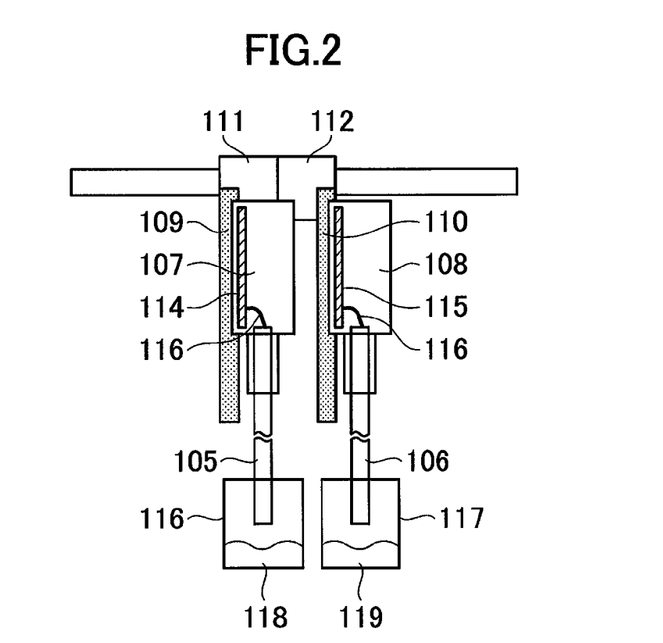
FIG. 2 is a diagram illustrating, in detail, reagent probe moving mechanisms of the automatic analyzer illustrated in FIG. 1.

FIG. 1 is a schematic diagram illustrating an overall configuration of an automatic analyzer to which the present invention is applied. FIG. 2 is a diagram illustrating, in detail, reagent probe moving mechanisms of the automatic analyzer illustrated in FIG. 1.

For simplicity of description, an example in which two reagent probes are provided is described.

In FIGS. 1 and 2, a sample probe 101 sucks a sample from a sample vessel 102 and dispenses the sample into a reaction vessel 104 placed on a reaction disk 103. A reagent probe 105 and a reagent probe 106 are held by a reagent holder 107 and a reagent probe holder 108, respectively and can be moved up and down by a moving mechanism 109 and a moving mechanism 110 in Z direction (vertical direction), respectively.

The moving mechanisms 109 and 110 can be moved by moving mechanisms 111 and 112 in X direction (horizontal direction) above an arbitrary reagent bottle 113 placed on a reagent disk 121 and above the reagent disk 103. A liquid level detector 114 and a liquid level detector 115 are held by the reagent probe holder 107 and the reagent probe holder 108, respectively and electrically connected to the reagent probe 105 and the reagent probe 106 by wirings 116, respectively. For example, cylindrical parts of the reagent probes 105 and 106 are electrode parts that are connected to the wirings 116.

After the reagent probes 105 and 106 are moved to positions located above reagent bottles 116 and 117 by the moving mechanisms 111 and 112, they are moved down by the moving mechanisms 109 and 110, respectively. When the reagent probe 105 and the reagent probe 106 contact liquid surfaces of a reagent 118 and a reagent 119 each stored in the reagent bottle 116 and in the reagent bottle 117, the liquid levels are detected by the liquid level detectors 114 and 115, respectively.

When the liquid detectors 114 and 115 detect the liquid levels, the moving mechanisms 109 and 110 stop operating, and the reagent probes 105 and 106 suck the reagents 118 and 119 into the reagent probes 105 and 106. After the sucking of the reagents 118 and 119, the reagent probes 105 and 106 are moved up by the moving mechanisms 109 and 110 and moved by the moving mechanisms 111 and 112 to positions located above the reaction disk 103 and discharge the reagents 118 and 119 into reaction vessels 104. The moving mechanisms 111 and 112 are held by a holding mechanism 122 and move along the holding mechanism 122.

After the sample stored in the sample vessel 102 reacts with the reagents 118 and 119 for a constant time period, a signal amount that corresponds to the concentration of a target substance is detected by a detector 120. The detector 120 serves as an analyzer that analyzes the target substance on the basis of the detected signal amount. An analyzer may be provided separately from the detector 120.

A plurality of reagent bottles 113 are arranged in the reagent disk 121. By rotating the reagent disk 121, an arbitrary reagent bottle 113 can be moved to a position under a trajectory of the moving mechanisms 111 and 112. Thus, the reagents can be sucked into the reagent probes 105 and 106 from arbitrary bottles 113. The moving mechanisms 109 and 110 can move the reagent probes 105 and 106 in Z direction at substantially the same time so that the reagent probes 105 and 106 suck the reagents from a plurality of reagent bottles located in the vicinity of the moving mechanisms 109 and 110. For example, if one reagent bottle 113 is configured by coupling a plurality of reagent vessels and has an opening portion for sucking for each of the reagent vessels, the reagent probes 105 and 106 simultaneously suck the reagents from the plurality of opening portions formed in the same reagent bottle 113. In addition, if many reagent bottles 113 are stored in the reagent disk 121, the reagent probes 105 and 106 simultaneously suck the reagents from reagent bottles 113 arranged adjacent to each other. In this case, there is a possibility that top ends of the reagent probes 105 and 106 may contact the liquid surfaces of the reagents at substantially the same time. In addition, the moving mechanism 109 and the moving mechanism 110 enable the reagent probe 105 and the reagent probe 106 to dispense the reagents into reagent bottles on a bottle basis.

Figure 3:
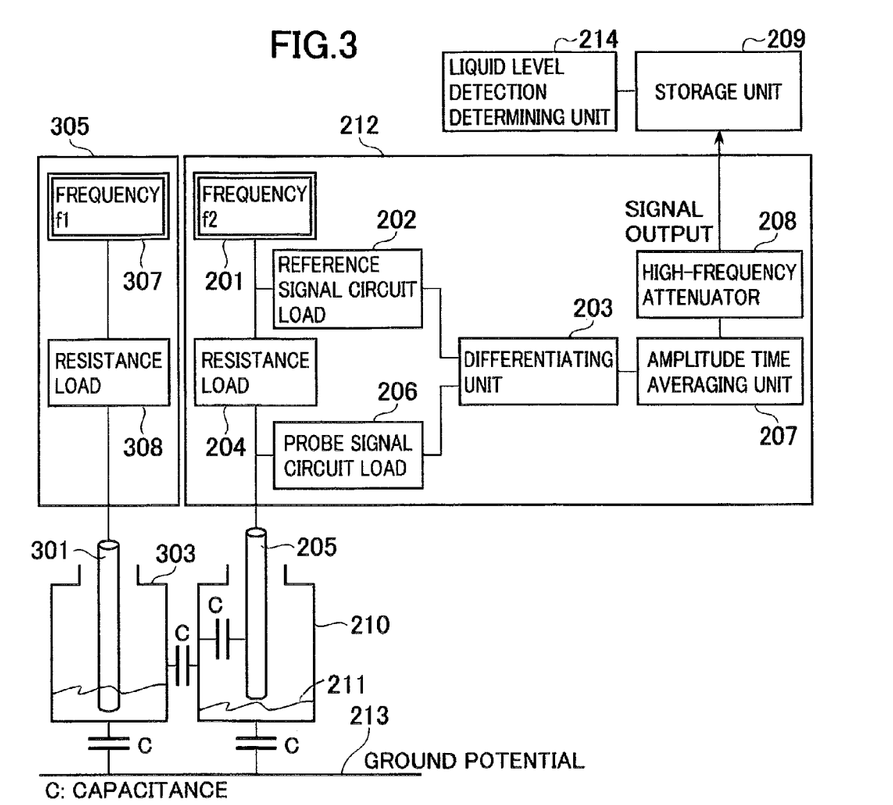
FIG. 3 is a diagram illustrating internal configurations of liquid level detectors 114 and 115 according to a first embodiment of the present invention.

FIG. 3 is a diagram illustrating internal configurations of the liquid level detectors 114 and 115 according to the first embodiment of the present invention. In FIG. 3, in order to simplify a description, an illustration of parts other than an oscillator 307 and resistance load 308 of the detector 114, a reagent probe 301, and a reagent bottle 303 is omitted. This is because of the fact that the detector 114 has the same configuration as the detector 115 and a description of the internal configuration of the detector 114 can be omitted by describing the internal configuration of the detector 115.

In FIG. 3, an oscillator 201 of a detector substrate 212 oscillates at an oscillation frequency f2 (Hz). An oscillation voltage is supplied from the oscillator 201 to a differentiating unit 203 through a reference signal circuit load 202 that outputs a reference signal (in a first path). In addition, the oscillation voltage is supplied from the oscillator 201 to a resistance load 204 and then to the reagent probe 205 and supplied to the differentiating unit 203 through a probe signal circuit load 206 (in a second path).

A top end of the reagent probe 205 reaches a liquid surface 211 of the reagent stored in a reagent bottle 210. In addition, the reagent bottle 210 is connected to a ground 213 through capacitance C. A phase difference due to the presence of the capacitance C occurs between a signal output from the reference signal circuit load 202 and a signal output from the probe signal circuit load 206.

After the differentiating unit 203 obtains the difference between an output of the first path and an output of the second path, a signal corresponding to a change in the capacitance C between the probe 205 and the ground 213 is obtained by causing an amplitude time averaging unit 207 to obtain an amplitude averaged over time.

The signal obtained by the amplitude time averaging unit 207 is supplied to a high-frequency attenuator 208 in order to reduce noise. The high-frequency attenuator 208 attenuates a high-frequency component caused by noise or static electricity. A signal that is output from the high-frequency attenuator 208 is supplied to a storage unit 209. A liquid level detection determining unit 214 determines, on the basis of the output signal supplied to the storage unit 209, whether or not the top end of the probe 205 has reached the liquid surface of the reagent. If the liquid level detection determining unit 214 determines that the top end of the probe 205 has reached the liquid surface, an operation of the moving mechanism 109 or 110 is stopped and an operation of moving down the probe 205 or 301 is stopped.

The storage unit 209 stores, on the basis of an instruction from the liquid detection determining unit 214, a value of an output signal obtained when the reagent probe 205 is moved up to a position located above the liquid surface 211 of the reagent stored in the reagent bottle 201 and a value of an output signal obtained when the reagent probe 205 is moved down and contacts the liquid surface 211 of the reagent.

Figure 4:
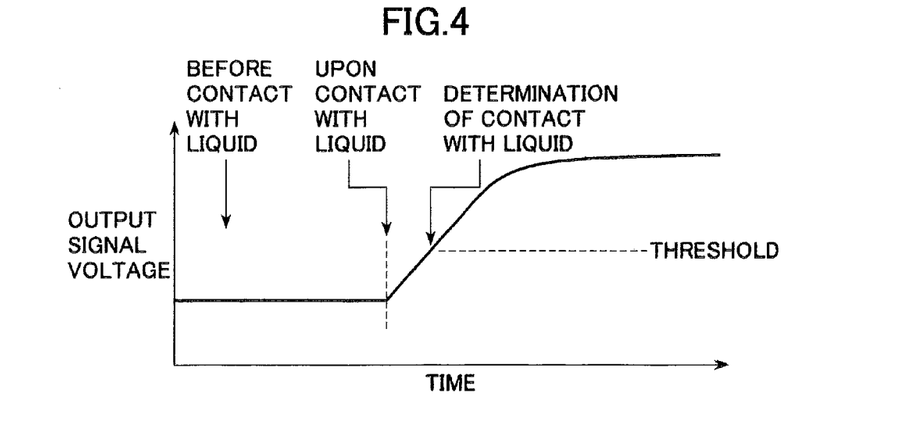
FIG. 4 is a diagram illustrating a change in a signal output from a high-frequency attenuator when a single probe is driven.
Figure 9:
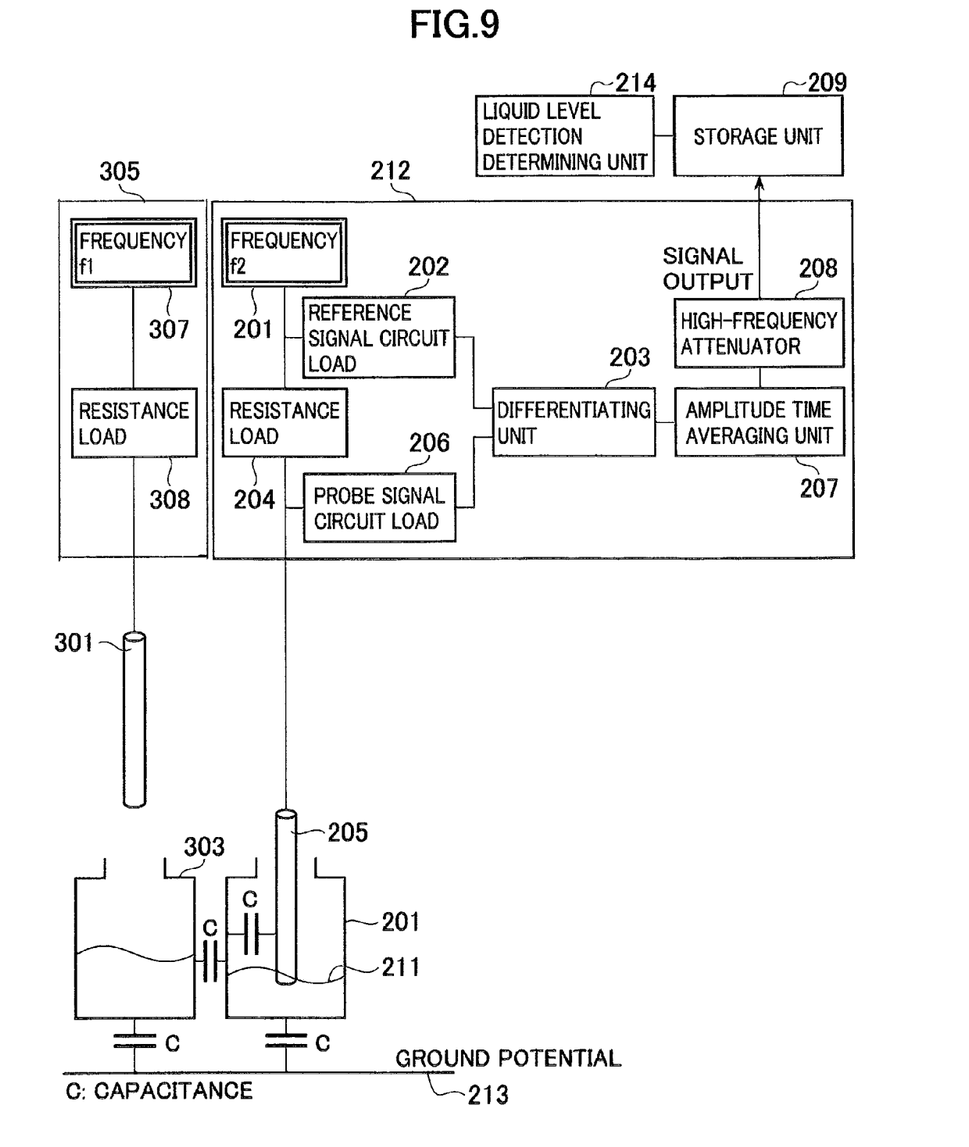
FIG. 9 is a diagram illustrating the internal configurations of the liquid level detectors according to the first embodiment of the present invention.

FIG. 9 illustrates the configurations in the case where the probe 301 is not moved in Z direction and only the probe 205 is moved in Z direction and contacts the liquid surface 211 of the reagent. A change in a signal output from the high-frequency attenuator 208 in this case is illustrated in FIG. 4. In FIG. 9, the liquid level detection determining unit 214 compares the levels of the signals output from the high-frequency attenuator 208 and stored. If a change between the levels is equal to or higher than a certain threshold, the liquid level detection determining unit 214 determines that the reagent probe 205 has contacted the liquid surface 211. The moving mechanism 109 or 110 stops the movement of the probe 205 on the basis of the determination. If only the probe 205 is moved, the waveform of the output signal voltage does not significantly pulsate as illustrated in FIG. 4, and whether or not the probe 205 has contacted the liquid surface of the reagent can be determined with high accuracy. Although the example in which only the probe 205 is moved is described, the same applies to the case where the probe 205 is not moved in Z direction and only the probe 301 is moved in Z direction.

In the example illustrated in FIG. 9, although the function of the detector substrate 212 includes from the unit 201 to the high-frequency attenuator 208, it may include those from the unit 201 previous to the differentiating unit 203 or to the liquid level detection determining unit 214. That is to say, the amplitude time averaging unit 207 and the high-frequency attenuator 208 may not be formed on the detector substrate 212 and may be arranged outside the detector substrate 212. Alternatively, the storage unit 209 and the liquid level detection determining unit 214 may be arranged on the detector substrate 212. In addition, the high-frequency attenuator 208 may be arranged between the reference signal circuit load 202 and the differentiating unit 203. Alternatively, the high-frequency attenuator 208 may be arranged between the probe signal circuit load 206 and the differentiating unit 203.

Stray capacitance C exists between the reagent probe 205 and the reagent bottle 210. Similarly, stray capacitance C exists between the reagent probe 301 and the reagent bottle 303. In addition, stray capacitance C exists between the reagent bottle 210 and the reagent bottle 303.

When the reagent probe 301 and the reagent probe 205 simultaneously perform the sucking operations, a detector substrate 305 and the detector substrate 212 are electrically connected to each other by the capacitance C between the reagent bottle 303 and the reagent bottle 210.

Figure 5:
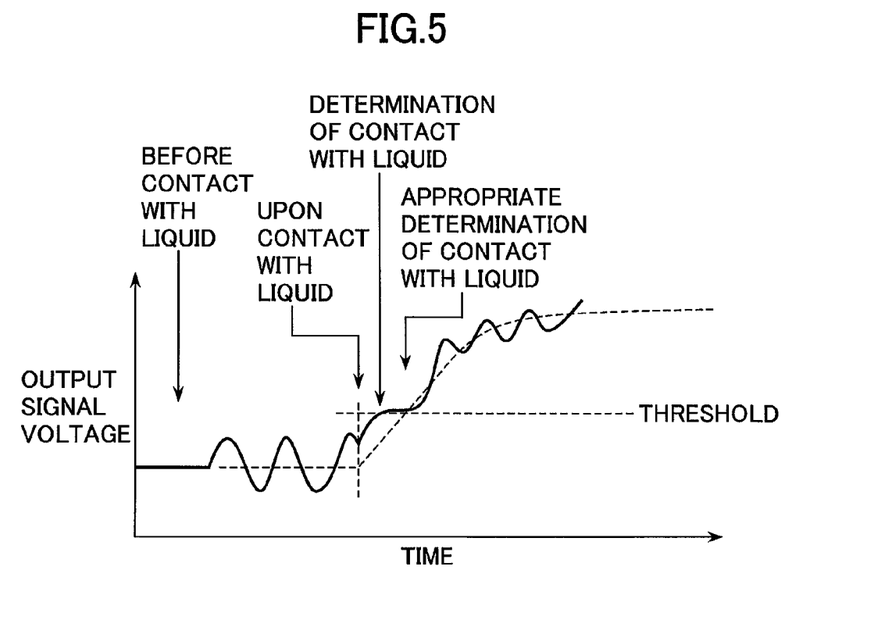
FIG. 5 is a diagram illustrating the waveform of a signal output from the high-frequency attenuator when the difference between frequencies f1 and f2 of detector oscillators for a plurality of probes is approximately several Hz.

The frequencies f1 and f2 of the detector oscillators 307 and 201 are originally equal to each other. The frequencies f1 and f2 may be different, however, by approximately several Hz from each other due to a variation in manufactured constituent parts. FIG. 5 is a diagram illustrating a signal waveform when the frequencies f1 and f2 of the detector oscillators 307 and 201 are different by approximately several Hz from each other.

In this case, as well as an actual change in the capacitance due to the contact of the reagent probes 301 and 205 with the liquid surfaces, a low-frequency oscillation waveform that has an amplitude value corresponding to the difference between the frequencies is added to the output signal voltage. Since the waveform of the output signal voltage pulsates, the output signal voltage exceeds the threshold to be used for the determination of the liquid surface contact, at a time different from an appropriate time at which the probes have contacted the liquid surfaces. As a result, it may be determined that the probes have contacted the liquid surfaces at inappropriate times before appropriate times when the probes contact the liquid surfaces.

Thus, since the times when the reagent probes 301 and 205 stop moving down may not be appropriate, the reagents may not be appropriately sucked, thereby degrading the dispensing accuracy.

Figure 6:
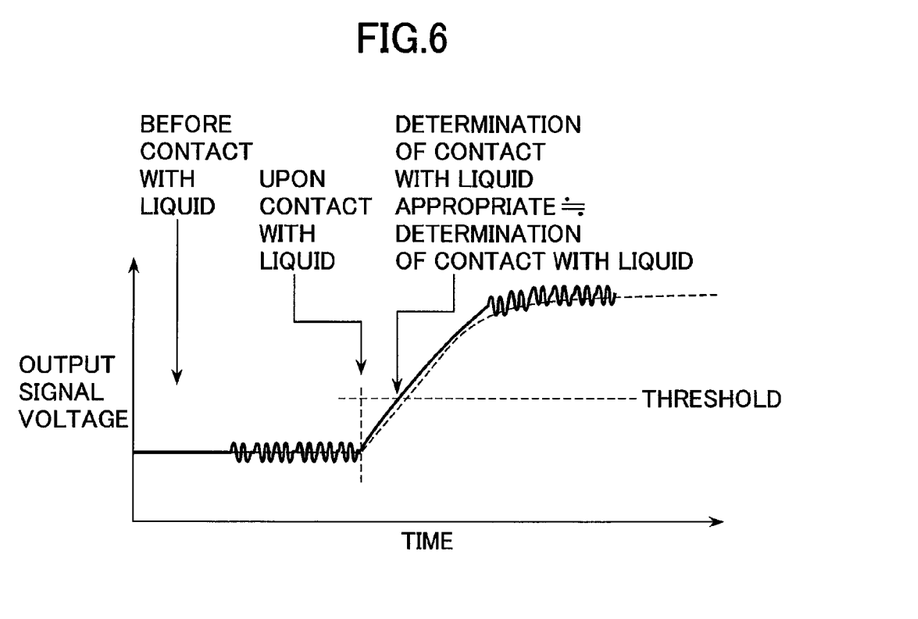
FIG. 6 is a diagram illustrating the waveform of a signal output from the high-frequency attenuator when the difference between the frequencies f1 and f2 of the detector oscillators for the plurality of probes is approximately several kHz.

FIG. 6 illustrates the waveform of an output signal when the frequency difference between the f1 and f2 of the detector oscillators 307 and 201 is intentionally set to be high as the degree of several kHz in the first embodiment of the present invention. In this case, as well as an actual change in the capacitance due to the contact with the liquid surfaces, a high-frequency oscillation waveform corresponding to the frequency difference between the f1 and f2 is added to the output signal voltage. Since an amplitude value of a high-frequency component can be attenuated by the high-frequency attenuator 208, however, the contact with the liquid surfaces can be appropriately determined.

Specifically, when the frequency difference between the f1 and f2 is several kHz, although a high-frequency signal component corresponding to the frequency difference is superimposed on the output signal voltage, the superimposed component can be attenuated by the high-frequency attenuator 208 that has been conventionally provided to remove noise. If the frequency difference between the f1 and f2 is set to be low as the degree of several Hz, the signal component to be superimposed on the signal voltage cannot be removed by the high-frequency attenuator 208. This is because of the fact that the existing high-frequency attenuator 208 cannot effectively attenuate a frequency component of approximately several Hz. In such a case, providing the frequency attenuator that removes the component of the frequency difference between the f1 and f2 and that does not remove signals indicating the contact with the liquid surfaces, the same effect as that described above can be achieved.

In the first embodiment of the present invention, since the frequency attenuator that removes the frequency difference between the f1 and f2 is provided, even when the probes dispense the reagents into reagent vessels at substantially the same time, the liquid levels of the reagents can be effectively determined. In addition, if the frequency difference between the f1 and f2 is set to several kHz, by utilizing the existing high-frequency attenuator 208 for reducing or removing noise, a reduction in the liquid level detection accuracy can be suppressed at the time when the plurality of probes are simultaneously used, and the simplicity of the configuration can be achieved.

Thus, the times when the probes are stopped can be appropriate times when the probes contact the liquid surfaces, and the automatic analyzer that has high dispensing accuracy can be achieved.

In the first embodiment of the present invention, since the amplitude of the oscillation waveform to be superimposed on the output signal can be small, the threshold to be used for the determination of the liquid level detection can be lowered, and the immersion depth of the probe's top end can be small. Thus, the amounts of liquids attached to the top ends of the probes can be reduced, thereby reducing contamination and the amount of a wasteful liquid.

Since impedance related to the capacitance can be represented by $1/(2\pi fC)$, a change in an output from a circuit that includes the capacitance is large. It is, therefore, preferable that the oscillation frequencies f be low as possible. The higher the frequencies f, however, the higher an attenuation effect of the high-frequency attenuator 208. Thus, if the high-frequency attenuator 208 remove noise caused by a frequency difference between the probes, it is preferable that the frequencies f of the oscillators be in a range from 1 kHz to several hundreds of kHz (and lower than 1000 kHz).

The difference between the frequencies f1 and f2 of the two oscillators is equal to or higher than cutoff frequencies of the high-frequency attenuators 208, and an upper limit of the difference is a value capable of ensuring gains of the reference signal circuit load 202 and probe signal circuit load 206.

Second Embodiment

Figure 7:
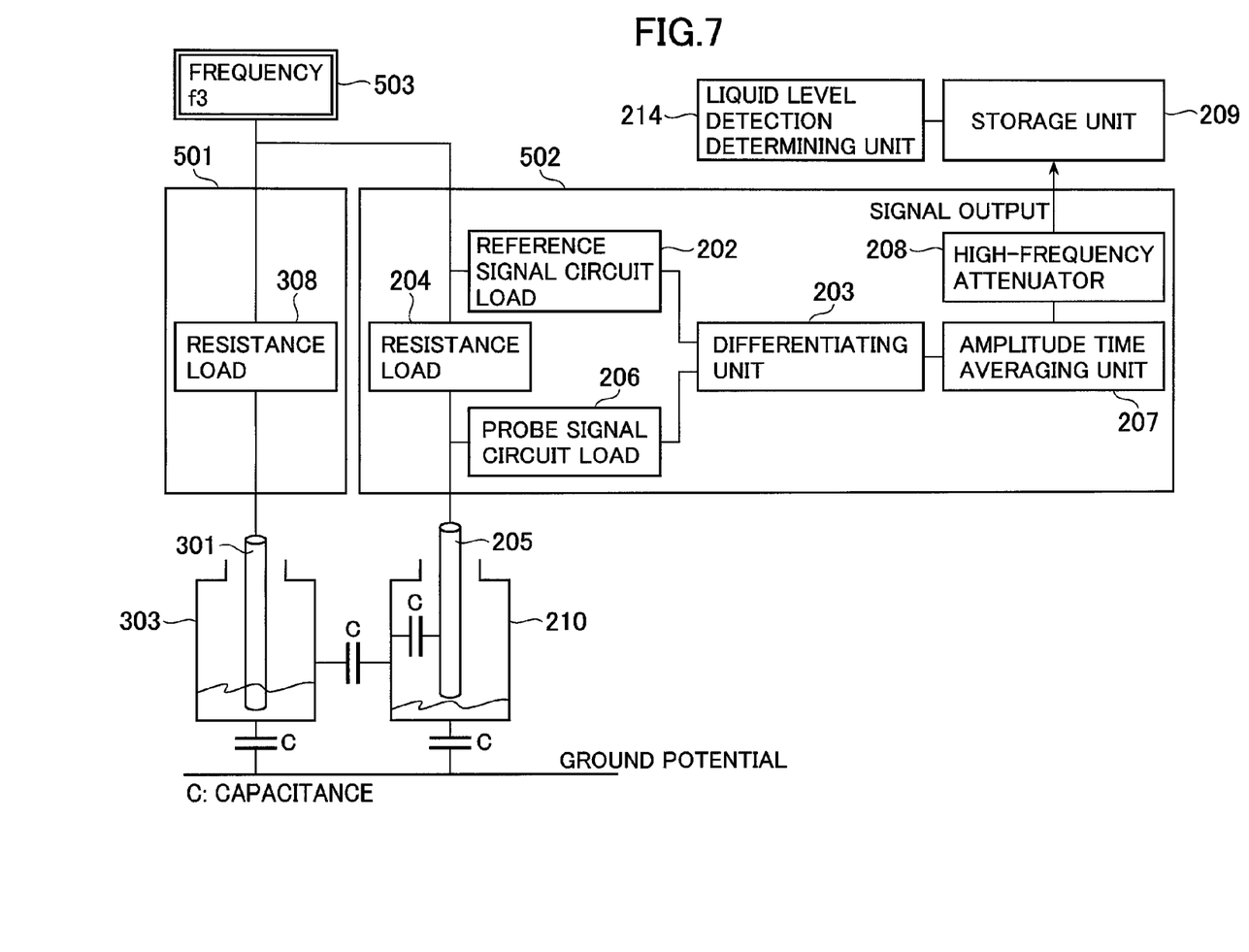
FIG. 7 is a diagram illustrating internal configurations of the liquid level detectors according to a second embodiment of the present invention.

FIG. 7 is a diagram illustrating internal configurations of the liquid level detectors according to the second embodiment of the present invention. An overall configuration according to the second embodiment of the present invention is the same as the example illustrated in FIG. 1, and an illustration thereof is omitted. The second embodiment is different from the first embodiment in that the oscillator 307 of the detector 114 and the oscillator 201 of the detector 115 are omitted, and a detector substrate 501 of the detector 114 and a detector substrate 502 of the detector 115 in the second embodiment have a oscillator 503 in common. Other configurations are the same as the example illustrated in FIG. 3.

In FIG. 7, when the reagent probe 205 and the reagent probe 301 simultaneously perform the sucking operations, the detector substrate 501 and the detector substrate 502 are electrically connected to each other by the capacitance C between the reagent bottle 303 and the reagent bottle 210.

Since a voltage signal is supplied to the probes 301 and 205 from the same oscillator 503, there is no difference between frequencies of signals output from the detectors 501 and 502.

Thus, the waveforms of output signal voltages obtained when the probes 301 and 205 suck the reagents are the same as the waveform (illustrated in FIG. 4) of the output signal obtained when the single reagent probe sucks the reagent. Thus, since such signal pulsation as illustrated in FIG. 5 does not occur, the times when the probes 301 and 205 contact the liquid surfaces can be appropriately determined, and the automatic analyzer that has high dispensing accuracy can be achieved.

So far as having an oscillator in common, the oscillator 503 may be arranged on the detector substrate 501 or the detector substrate 502.

Third Embodiment

Figure 8:
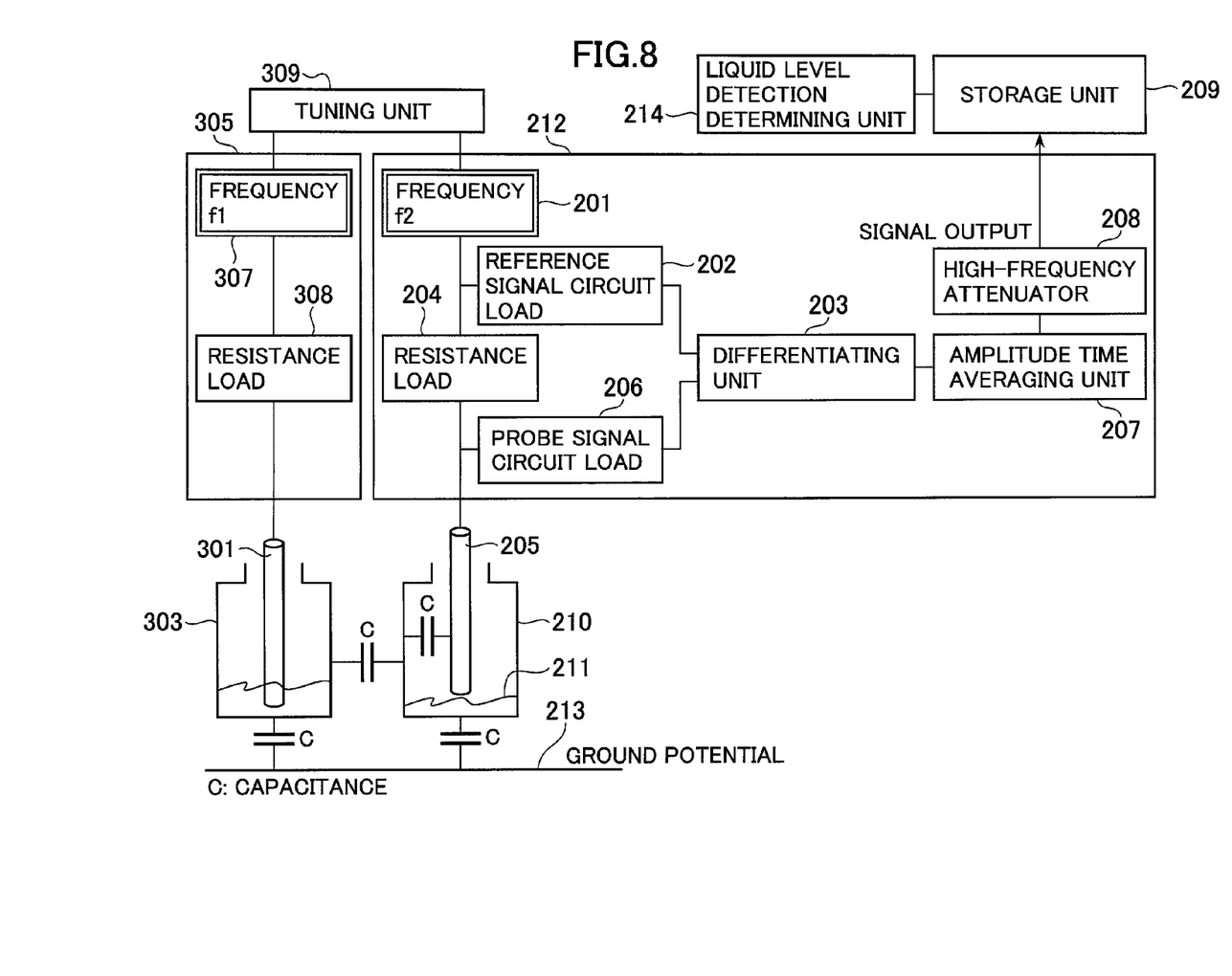
FIG. 8 is a diagram illustrating internal configurations of the liquid level detectors according to a third embodiment of the present invention.

FIG. 8 is a diagram illustrating internal configurations of the liquid level detectors 114 and 115 according to the third embodiment of the present invention. The example illustrated in FIG. 8 is the same as the example illustrated in FIG. 3, and, for simplicity of description, illustration of the parts other than the oscillator 307 and resistance load 308 of the detector 114, the reagent probe 301, and the reagent bottle 303 is omitted. An overall configuration according to the third embodiment of the present invention is the same as the example illustrated in FIG. 1, and an illustration thereof is omitted. The third embodiment is different from the first embodiment in that the oscillation frequencies f1 and f2 of the oscillators 307 and 201 are set to the same value as each other, which are tunable, and is that the third embodiment is added with a tuning unit 309.

Although the oscillation frequencies f1 and f2 are originally equal to each other, they may be different by approximately several Hz from each other due to a variation in manufactured constituent parts. Thus, the tuning unit 309 tunes the oscillation frequency f1 of the oscillator 307 and the oscillation frequency f2 of the oscillator 201 so that the tuned frequencies f1 and f2 are equal to a constant frequency f.

In the third embodiment of the present invention, since the tuning unit 309 adjusts the frequencies f1 and f2 to the same frequency as each other, the configuration can be achieved, in which a reduction in the liquid level detection accuracy due to simultaneous use of the plurality of probes is suppressed.

Thus, the times when the probes are stopped can be appropriate times when the probes contact the liquid surfaces, and the automatic analyzer that has high dispensing accuracy can be achieved.

In the aforementioned examples, the present invention is applied to the reagent dispensing probes. The present invention, however, is applicable to sample probes. If the present invention is applied to the sample probes, the reagent probes 205 and 301 illustrated in FIG. 3 are used as the sample probes, the reagent vessels 303 and 210 are used as sample vessels, and other configurations are similar to or the same as the configurations described above.

DESCRIPTION OF REFERENCE NUMERALS

101 . . . Sample probe, 102 . . . Sample, 103 . . . Reaction disk, 104 . . . Reaction vessel, 105, 106 . . . Reagent probe, 107, 108 . . . Reagent probe holder, 109, 110, 111, 112 . . . Moving mechanism, 113 . . . Reagent bottle, 114, 115 . . .

Liquid level detector, 116, 117 . . . Reagent bottle, 118, 119 . . . Reagent, 120 . . . Detector, 121 . . . Reagent disk, 122 . . . Holding mechanism, 201, 307 . . . Oscillator, 202 . . . Reference signal circuit load, 203 . . . Differentiating unit, 204 . . . Resistance load, 205, 301 . . . Reagent probe, 206 . . . Ground, 207 . . . Amplitude time averaging unit, 208 . . . High-frequency attenuator, 210, 303 . . . Reagent bottle, 211 . . . Liquid surface, 212 . . . Detector substrate, 305 . . . Liquid level detector substrate, 307 . . . Oscillator, 308 . . . Resistance load, 309 . . . Tuning unit, 501, 502 . . . Liquid level detector substrate, 503 . . . Oscillator

The invention claimed is:

1. An automatic analyzer that analyzes a plurality of samples comprising:
   a plurality of dispensing probes each configured to dispense liquid samples or liquid reagents;
   a plurality of vertical moving mechanisms that are each provided for each of the plurality of dispensing probes and that move up and down the plurality of dispensing probes;
   a plurality of oscillators that are each configured to supply, to a dispensing probe of the plurality of dispensing probes, individually, alternating voltages having a specific frequency difference therebetween;
   frequency attenuators that are each provided for each of the plurality of oscillators and are configured to attenuate the specific range of frequency components caused by alternating voltages at the dispensing probes; and
   liquid level detection determining units that are each provided for each of the plurality of dispensing probes and are configured to determine, from voltage changes caused by the plurality of probes contacting liquid, whether or not the dispensing probes have contacted liquid surfaces of the liquid samples or the liquid reagents based on signals output from the frequency attenuators, the liquid level detection determining units configured to stop the movement operations of the vertical moving mechanisms when the liquid level detection determining units determine that the dispensing probes have contacted the liquid surfaces.

2. The automatic analyzer according to claim 1,
   wherein the difference between the oscillation frequencies of the oscillators is equal to or greater than 1 kHz and less than 1000 kHz.

\* \* \* \* \*